(12) United States Patent
Campbell

(10) Patent No.: US 9,937,086 B2
(45) Date of Patent: Apr. 10, 2018

(54) DIAPER CHANGING SYSTEM

(71) Applicant: Alexandria N. Campbell, Lake Balboa, CA (US)

(72) Inventor: Alexandria N. Campbell, Lake Balboa, CA (US)

(*) Notice: Subject to any disclaimer, the term of this patent is extended or adjusted under 35 U.S.C. 154(b) by 283 days.

(21) Appl. No.: 15/041,185

(22) Filed: Feb. 11, 2016

(65) Prior Publication Data
US 2017/0231841 A1 Aug. 17, 2017

(51) Int. Cl.
*A61F 13/15* (2006.01)
*A61F 13/84* (2006.01)
*A61F 13/49* (2006.01)
*A61F 13/551* (2006.01)

(52) U.S. Cl.
CPC .............. *A61F 13/84* (2013.01); *A61F 13/49* (2013.01); *A61F 13/5511* (2013.01); *A61F 13/5512* (2013.01); *A61F 13/5519* (2013.01); *A61F 13/55115* (2013.01); *A61F 2013/55125* (2013.01); *A61F 2013/8402* (2013.01); *A61F 2013/8476* (2013.01)

(58) Field of Classification Search
CPC ...... A61F 13/84; A61F 13/49; A61F 13/5511; A61F 13/55115; A61F 13/5512; A61F 13/5519; A61F 2013/55125; A61F 2013/8402; A61F 2013/8476
USPC ....................................... 604/385.06, 385.13
See application file for complete search history.

(56) References Cited

U.S. PATENT DOCUMENTS

| 3,875,942 A * | 4/1975 | Roberts ................. A61F 13/512 604/370 |
| 4,623,339 A * | 11/1986 | Ciraldo ................... A61F 13/84 604/359 |
| 4,808,175 A | 2/1989 | Hansen |
| 5,582,605 A | 12/1996 | Lepie |
| 6,454,748 B1 | 9/2002 | Ives |
| 2012/0046631 A1 | 2/2012 | B. et al. |
| 2013/0204220 A1 | 8/2013 | Gunter |

* cited by examiner

*Primary Examiner* — Jacqueline Stephens

(57) ABSTRACT

A diaper changing system for efficiently changing a diaper without having to carry a diaper bag. The diaper changing system generally includes a diaper having an exterior surface and an interior surface, a cavity beneath the interior surface, a plurality of dispensing openings extending through the interior surface to fluidly connect to the cavity, and a receiver opening extending through the interior surface to fluidly connected to the cavity. The receiver opening is adapted to removably receive a nozzle of a cream container to receive a cream for insertion into the cavity and later dispensing from the cavity through the dispensing openings to the skin of the baby. A bag is removably attached to the exterior surface of the diaper for storing the cream container and wipes until used. The bag is removed and used as a garbage container when the diaper is used.

20 Claims, 6 Drawing Sheets

DIAPER CHANGING SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

Field of the Invention

The present invention relates generally to a diaper and more specifically it relates to a diaper changing system for efficiently changing a diaper without having to carry a diaper bag.

Description of the Related Art

Any discussion of the related art throughout the specification should in no way be considered as an admission that such related art is widely known or forms part of common general knowledge in the field.

Disposable diapers have been used for years for babies (e.g. newborns, infants and toddlers). While disposable diapers are useful and convenient for changing a soiled diaper, a parent still has to bring along a separate diaper bag that has various items such as diaper cream, wipes and related items to clean and prepare the baby prior to attaching the new diaper. Furthermore, once the soiled diaper is removed the caregiver needs to find a garbage and if a garbage is not nearby they have to keep the soiled diaper until a garbage can be found. In addition, when changing a diaper the caregiver often times will apply diaper cream to the baby resulting in the diaper cream being stuck to their fingers and under their nails resulting in an undesirable smell for the caregiver. In addition, it is time consuming to open the diaper bag, remove the contents, change the diaper, replace the contents to the diaper bag and find a nearby garbage container.

Because of the inherent problems with the related art, there is a need for a new and improved diaper changing system for efficiently changing a diaper without having to carry a diaper bag.

BRIEF SUMMARY OF THE INVENTION

Provided herein is a diaper which includes a diaper having an exterior surface and an interior surface, a cavity beneath the interior surface, a plurality of dispensing openings extending through the interior surface to fluidly connect to the cavity, and a receiver opening extending through the interior surface to fluidly connected to the cavity. The receiver opening is adapted to removably receive a nozzle of a cream container to receive a cream for insertion into the cavity and later dispensing from the cavity through the dispensing openings to the skin of the baby. A bag is removably attached to the exterior surface of the diaper for storing the cream container and wipes until used. The bag is removed and used as a garbage container when the diaper is used.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
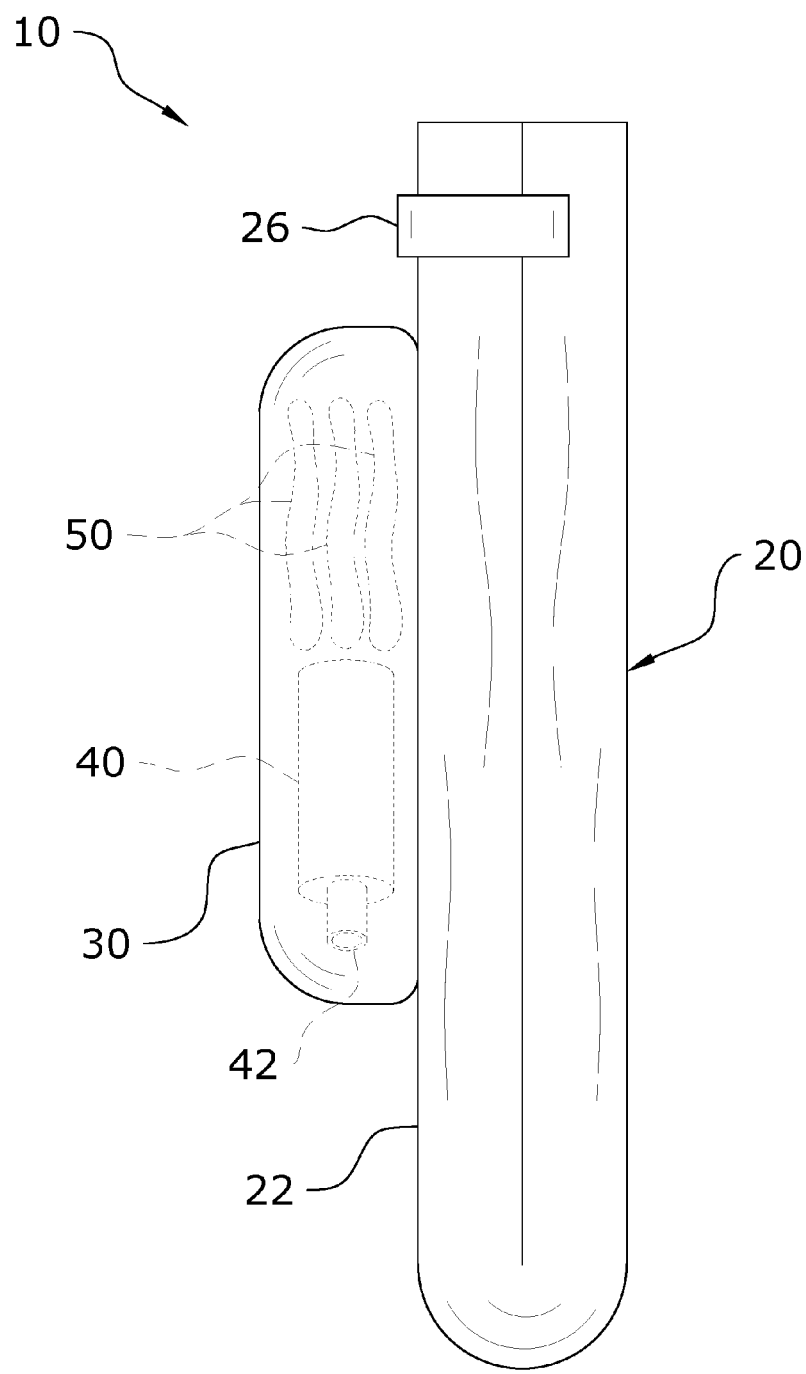
FIG. 1 is a side view of the present invention.

A. Overview.

Turning now descriptively to the drawings, in which similar reference characters denote similar elements throughout the several views, FIGS. 1 through 7 illustrate a diaper changing system 10, which comprises a diaper 20 having an exterior surface 22 and an interior surface 24, a cavity 62 beneath the interior surface 24, a plurality of dispensing openings 64 extending through the interior surface 24 to fluidly connect to the cavity 62, and a receiver opening 60 extending through the interior surface 24 to fluidly connected to the cavity 62. The receiver opening 60 is adapted to removably receive a nozzle 42 of a cream container 40 to receive a cream 44 for insertion into the cavity 62 and later dispensing from the cavity 62 through the dispensing openings 64 to the skin of the baby. A bag 30 is removably attached to the exterior surface 22 of the diaper 20 for storing the cream container 40 and wipes 50 until used. The bag 30 is removed and used as a garbage container when the diaper 20 is used.

B. Diaper.

FIGS. 1 through 4 illustrate an exemplary diaper 20. The diaper 20 has an exterior surface 22 and an interior surface 24 as illustrated in FIGS. 1 through 6 of the drawings. The interior surface 24 is positionable adjacent the skin of a baby. The base structure of the diaper 20 may be comprised of any type of conventional diaper 20 such as, but not limited to, a disposable diaper 20. The diaper 20 also includes two or more fasteners 26 (e.g. adhesive tape) as illustrated in FIGS. 1 through 4 of the drawings.

C. Cream Receiver and Dispenser.

Figure 3:
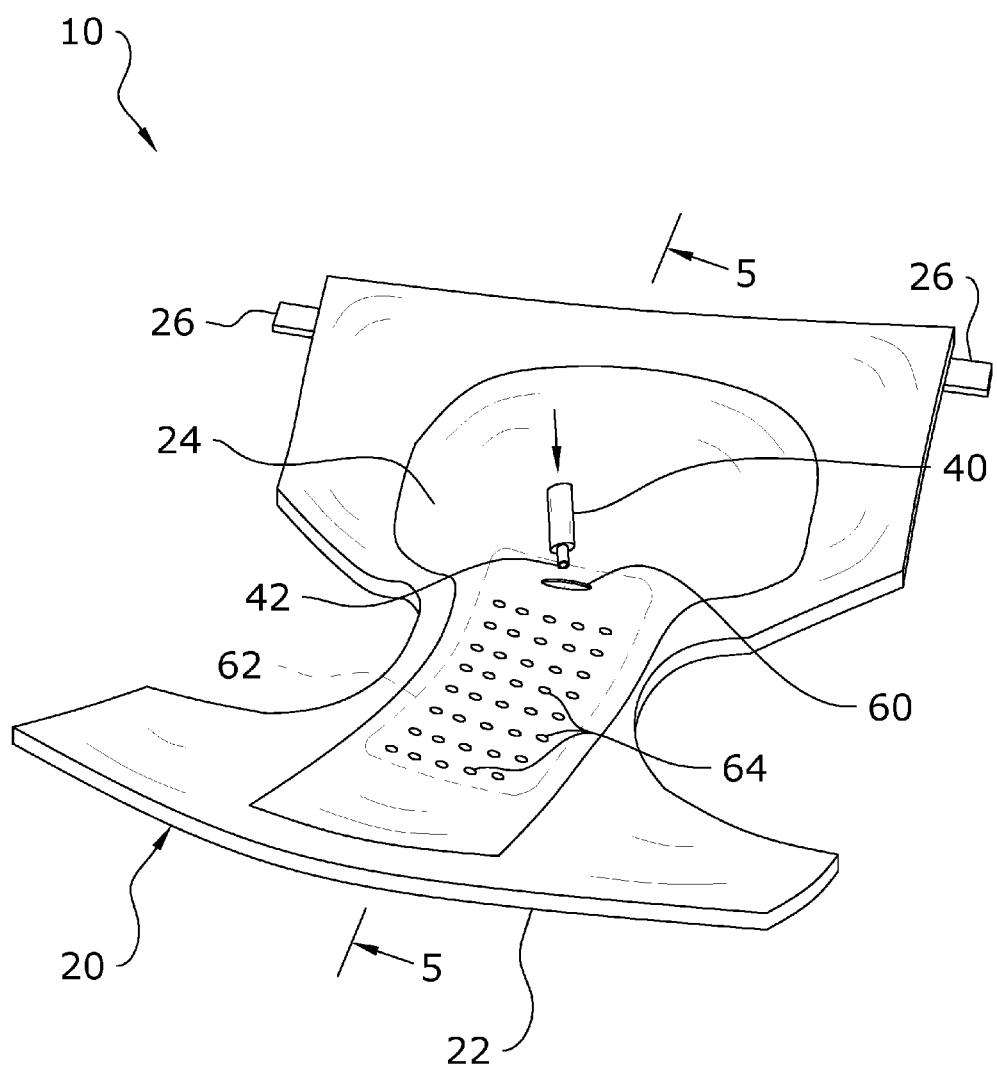
FIG. 3 is an upper perspective view of the diaper opened and the cream container inserted into the receiver opening.
Figure 4:
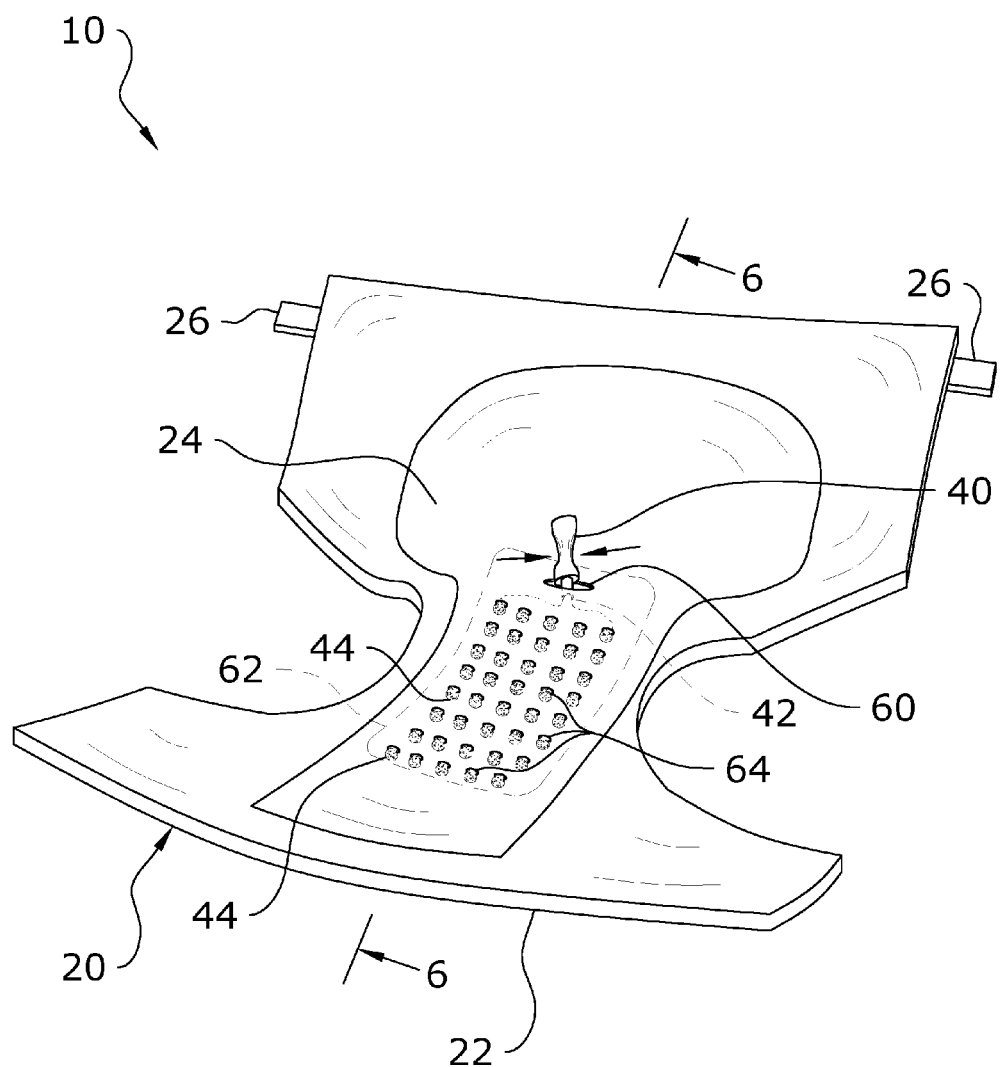
FIG. 4 is an upper perspective view of the diaper opened and the cream container inserted into the receiver opening with the cream container being squeezed to dispense the cream into the cavity of the diaper.
Figure 5:
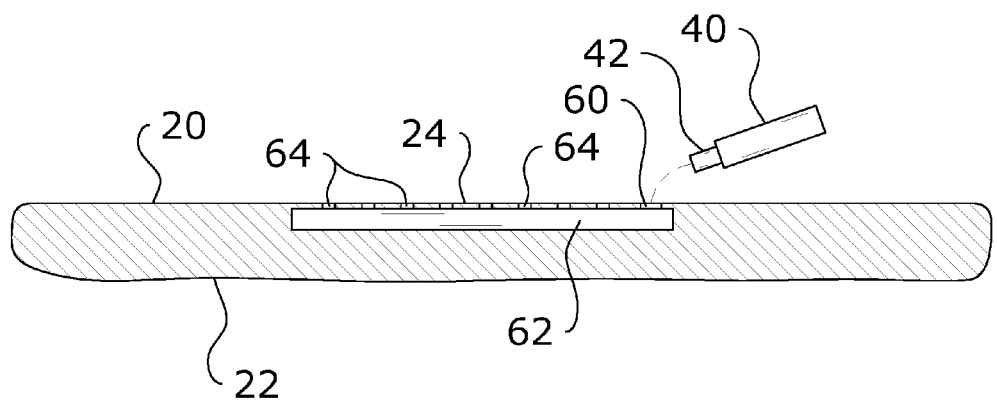
FIG. 5 is a cross sectional view taken along line 5-5 of FIG. 3.

A cavity 62 is positioned beneath the interior surface 24 of the diaper 20 as illustrated in FIGS. 3 through 6 of the drawings. The cavity 62 is adapted to receive and dispense the cream 44 (e.g. diaper 20 cream) received from the cream container 40. The cavity 62 preferably extends along a central portion of the interior surface 24 as illustrated in FIGS. 3 and 4. The cavity 62 is comprised of a flat structure that extends along the portion of the interior surface 24 that corresponds to and is adjacent to the portion of the body of the baby that the cream 44 is to be applied to after the diaper 20 is attached to the baby.

The portion of the interior surface 24 positioned above the cavity 62 is permeable to allow for the dispensing of the cream 44 from within the cavity 62 to outside of the interior surface 24 of the diaper 20. It is preferably that a plurality of dispensing openings 64 extend through the interior surface 24 of the diaper 20 as illustrated in FIGS. 3 through 6 of the drawings. The dispensing openings 64 are fluidly connected to the cavity 62 to dispense the cream 44 to the skin of the baby that is adjacent the interior surface 24. The dispensing openings 64 preferably cover a significant portion of the cavity 62 to ensure an even distribution of the cream 44 to the baby when the diaper 20 is secured to the baby as illustrated in FIGS. 3 through 6 of the drawings.

The cavity 62 has a first end, a second end and a longitudinal axis extending from the first end to the second end as illustrated in FIGS. 3 and 4. The receiver opening 60 is preferably adjacent the first end or the second end but may be positioned between the first end and second end. The dispensing openings 64 may be aligned in a plurality of rows that are transverse with respect to the longitudinal axis as further illustrated in FIGS. 3 and 4 of the drawings.

A receiver opening 60 extends through the interior surface 24 of the diaper 20 and is fluidly connected to the cavity 62 to allow for filling of the cavity 62 with cream 44 from the cream container 40. The receiver opening 60 is preferably larger in size than the dispensing openings 64 and is adapted to removably receive the nozzle 42 of the cream container 40 for receiving the cream 44 from the cream container 40. As illustrated in FIGS. 3 and 4, the receiver opening 60 may be positioned near the back portion of the diaper 20. However, the receiver opening 60 may be positioned near the front portion, the middle portion or other portions of the diaper 20.

D. Bag and Contents.

A bag 30 is attached to the exterior surface 22 or the interior surface 24 of the diaper 20. The bag 30 is preferably comprised of a plastic material but may be comprised of various other materials. The bag 30 has an upper opening to receive various items after it is removed from the diaper 20.

Figure 2:
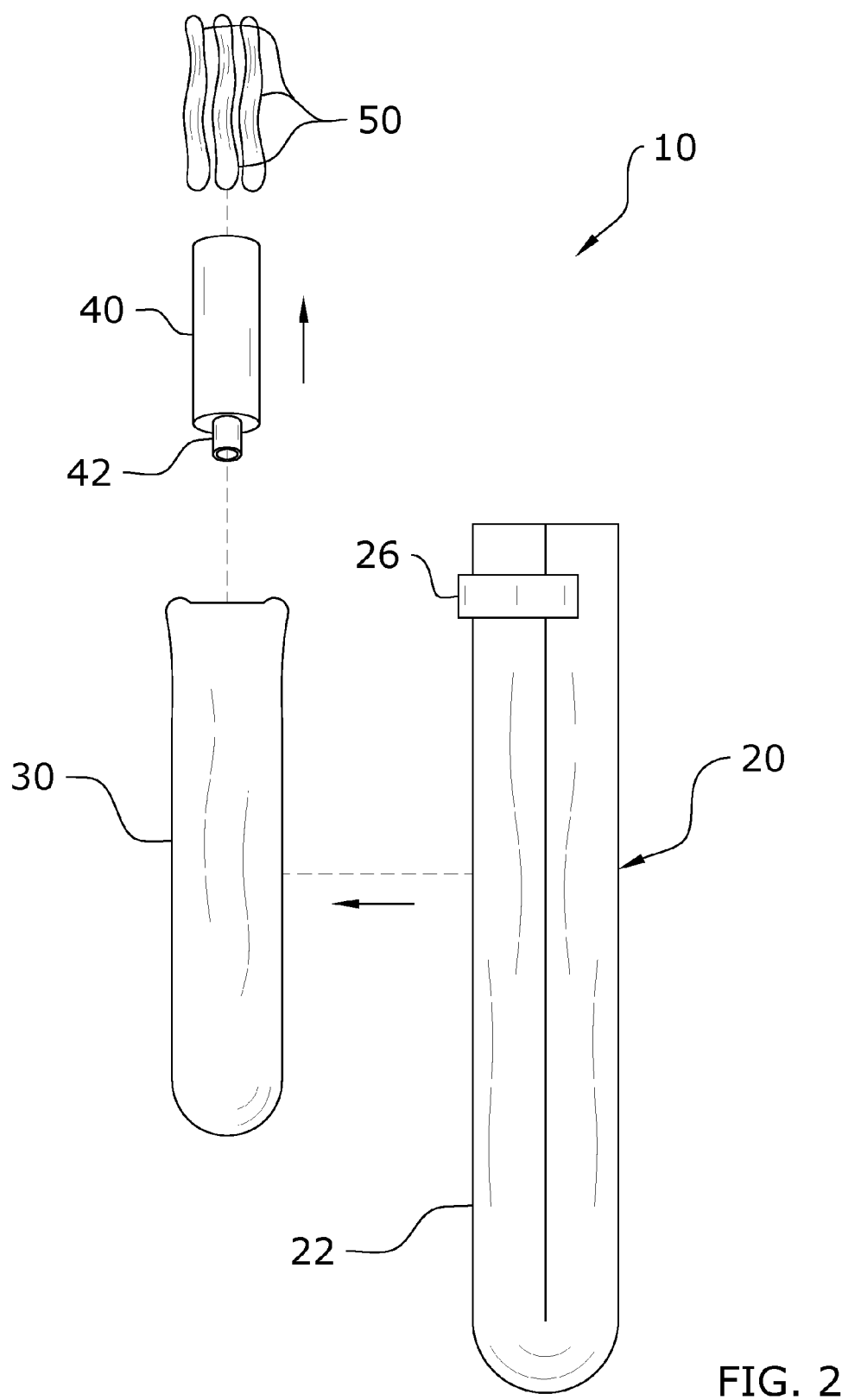
FIG. 2 is a side view of the present invention with the bag removed.

The bag 30 is preferably removably attached to the exterior surface 22 of the diaper 20 as illustrated in FIGS. 1 and 2 of the drawings. Various types of attachment structures may be used to removably attach a portion of the bag 30 to the exterior surface 22 of the diaper 20 such as, but not limited to, adhesive. When the bag 30 is attached to the diaper 20, the bag 30 preferably stores one or more removable items used in changing a soiled diaper 20 such as, but not limited to, a cream container 40 and one or more wipes 50.

The cream container 40 has a nozzle 42 that may have a cap or other sealing device to prevent accidental discharge of the cream 44 from the cream container 40. The cream container 40 stores and dispenses the fluid material 44 through the nozzle 42. For example, the fluid material may be comprised of, but not limited to, a cream, a medicated cream, a non-medicated cream, diaper cream, medicated diaper cream or other fluid material. The cream container 40 is preferably comprised of a compressible container that may be squeezed by a user to discharge the cream 44 into the cavity 62 of the diaper 20. The nozzle 42 of the cream container 40 is formed to fit within the receiver opening 60 in a removable manner. The nozzle 42 is preferably sized to be easily fit within the receiver opening 60 while still retaining a substantial seal between the nozzle 42 and the receiver opening 60 during filling of the cavity 62 with the cream 44.

One or more wipes 50 are preferably positioned within the bag 30 as illustrated in FIGS. 1 and 2 of the drawings. The wipes 50 may be comprised of various cleaning devices such as, but not limited to towels, wet wipes 50 and the like. The wipes 50 may include their own sealed containers that are opened to access the wipe within. The wipes 50 may be sealed in a single sealed package or in a plurality of individual sealed packages.

G. Operation of Preferred Embodiment.

Figure 6:
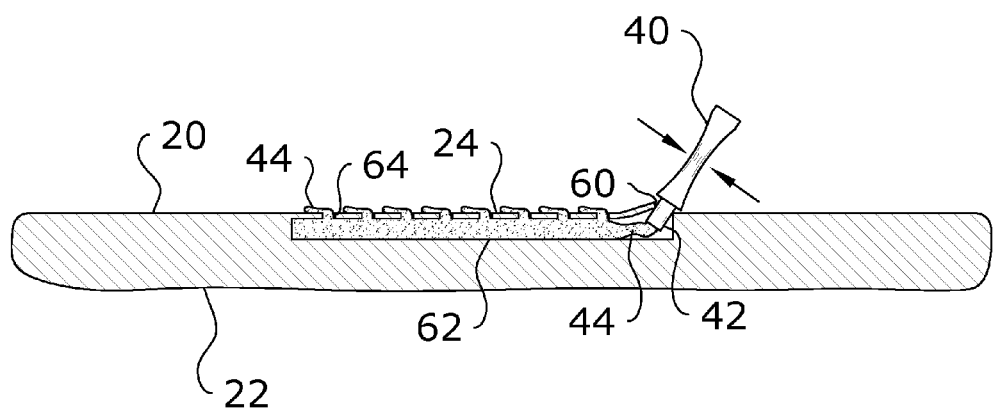
FIG. 6 is a cross sectional view taken along line 6-6 of FIG. 4.
Figure 7:
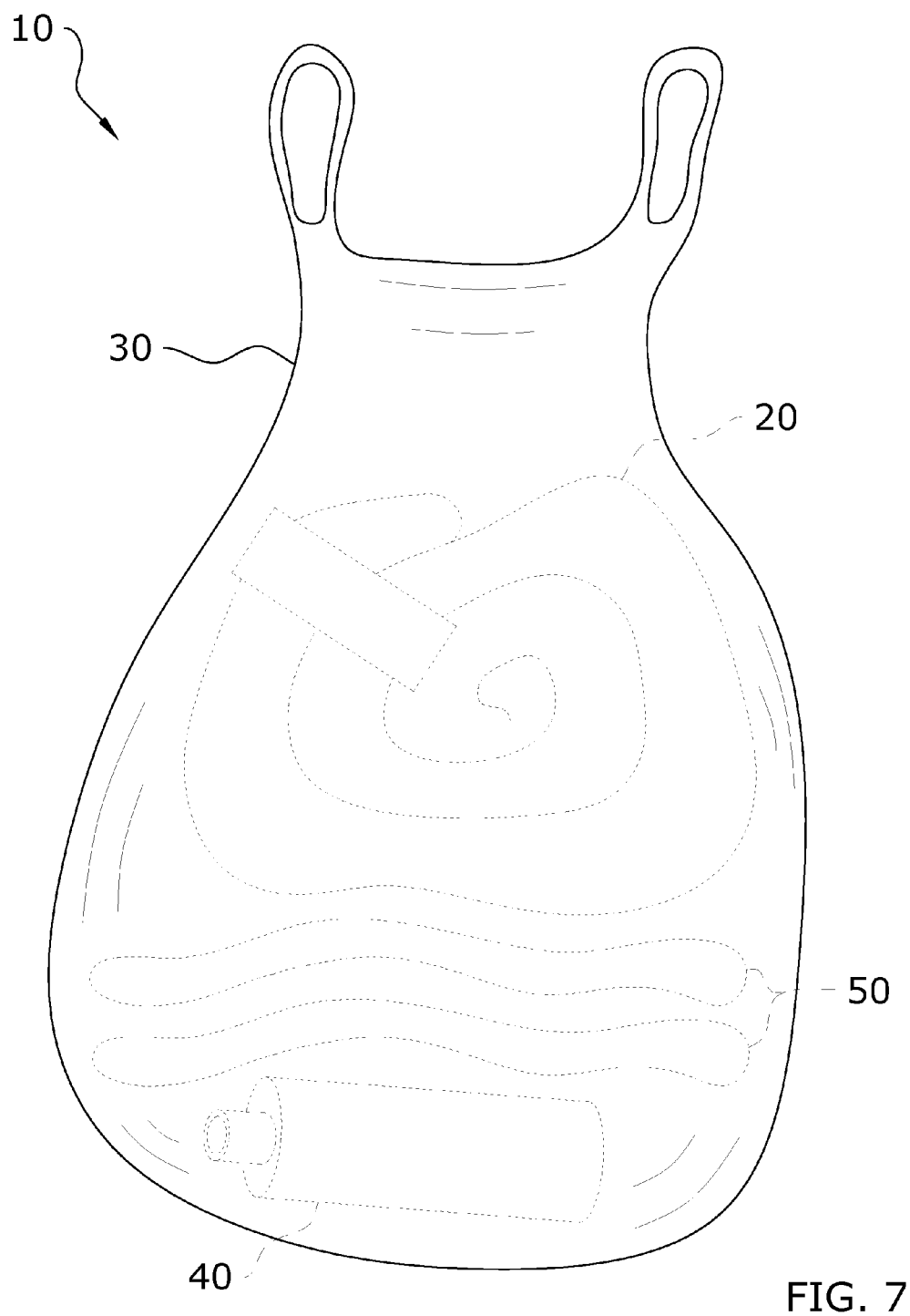
FIG. 7 is a side view of the bag with the garbage items positioned inside.

In use, the diaper 20 is initially folded with the bag 30 containing the cream container 40, wipes 50 and any other changing items as illustrated in FIG. 1. When a diaper 20 on a baby becomes soiled and needs to be changed, the caregiver removes the bag 30 from the new diaper 20 and removes the items (e.g. cream container 40, wipes 50, etc.) from the bag 30 needed to clean and prepare the baby. The caregiver removes the wipes 50 from their containers, removes the soiled diaper 20 from the baby and wraps the soiled diaper 20 upon itself to contain the soiled contents. The caregiver uses the wipes 50 to clean the baby. The caregiver then inserts the nozzle 42 of the cream container 40 into the receiver opening 60 of the diaper 20 and squeezes the cream container 40 to dispense the cream 44 through the receiver opening 60 into the cavity 62 as illustrated in FIG. 6 of the drawings. After the contents of the cream 44 are dispensed, the caregiver positions the new diaper 20 on the baby and secures with the fasteners 26 about the baby as a conventional diaper 20 would be attached. After the diaper 20 is attached to the baby, the weight of the baby presses upon the interior surface 24 thereby squeezing the cream 44 out of the cavity 62 through the dispensing openings 64 as shown in FIG. 6. After the cream 44 has been dispensed from the cavity 62, the cream 44 then comes in contact with the adjacent skin of the baby to treat and prevent various skin conditions such as diaper rash. The caregiver then inserts the used wipes 50, the soiled diaper 20 and the emptied cream container 40 along with any other pieces of garbage into the bag 30 as shown in FIG. 7. The caregiver then secures and closes the upper opening of the bag 30 in a sealed manner to prevent removal of the items within and to prevent odors from escaping the bag 30. The bag 30 with the garbage items may then be dispensed into a garbage container at any time.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A diaper changing system, comprising:
    a diaper having an exterior surface and an interior surface, wherein the interior surface is positionable adjacent the skin of a baby;
    a cavity positioned beneath the interior surface, wherein the cavity is adapted to receive and dispense a cream or other fluid material;
    a plurality of dispensing openings extending through the interior surface of the diaper, wherein the dispensing openings are fluidly connected to the cavity to dispense the cream to the skin of the baby; and
    a receiver opening extending through the interior surface of the diaper, wherein the receiver opening is fluidly connected to the cavity and wherein the receiver opening is adapted to receive a nozzle of a cream container for receiving the cream from the cream container.

2. The diaper changing system of claim 1, wherein the receiver opening is larger in size than the dispensing openings.

3. The diaper changing system of claim 1, wherein the cavity has a first end, a second end and a longitudinal axis extending from the first end to the second end, wherein the receiver opening is adjacent the first end or the second end.

4. The diaper changing system of claim 3, wherein the receiver opening is near a back portion of the diaper.

5. The diaper changing system of claim 3, wherein the dispensing openings are aligned in a plurality of rows that are transverse with respect to the longitudinal axis.

6. The diaper changing system of claim 1, wherein the cavity is comprised of a flat structure.

7. The diaper changing system of claim 1, wherein the receiver opening is adapted to removably receive the nozzle of the cream container.

8. A diaper changing system, comprising:
    a diaper having an exterior surface and an interior surface, wherein the interior surface is positionable adjacent the skin of a baby;
    a bag attached to the diaper;
    a cream container having a nozzle positioned within the bag, wherein the cream container stores and dispenses a cream;
    a cavity positioned beneath the interior surface, wherein the cavity is adapted to receive and dispense the cream or other fluid material;
    a plurality of dispensing openings extending through the interior surface of the diaper, wherein the dispensing openings are fluidly connected to the cavity to dispense the cream to the skin of the baby; and
    a receiver opening extending through the interior surface of the diaper, wherein the receiver opening is fluidly connected to the cavity and wherein the receiver opening is adapted to removably receive the nozzle of the cream container for receiving the cream from the cream container.

9. The diaper changing system of claim 8, wherein the bag is removably attached to the diaper.

10. The diaper changing system of claim 8, wherein the bag is attached to the exterior surface of the diaper.

11. The diaper changing system of claim 10, wherein the bag is removably attached to the exterior surface of the diaper.

12. The diaper changing system of claim 8, including a towel positioned within the bag.

13. The diaper changing system of claim 12, wherein the towel is comprised of a wet wipe.

14. The diaper changing system of claim 8, including a plurality of wet wipes positioned within the bag.

15. The diaper changing system of claim 8, wherein the receiver opening is larger in size than the dispensing openings.

16. The diaper changing system of claim 8, wherein the cavity has a first end, a second end and a longitudinal axis extending from the first end to the second end, wherein the receiver opening is adjacent the first end or the second end.

17. The diaper changing system of claim 16, wherein the receiver opening is near a back portion of the diaper.

18. The diaper changing system of claim 16, wherein the dispensing openings are aligned in a plurality of rows that are transverse with respect to the longitudinal axis.

19. The diaper changing system of claim 8, wherein the cavity is comprised of a flat structure.

20. A diaper changing system, comprising:
    a diaper having an exterior surface and an interior surface, wherein the interior surface is positionable adjacent the skin of a baby;
    a bag removably attached to the exterior surface of the diaper;
    a cream container having a nozzle positioned within the bag, wherein the cream container stores and dispenses a cream;
    a cavity positioned beneath the interior surface, wherein the cavity is adapted to receive and dispense the cream or other fluid material;
    a plurality of dispensing openings extending through the interior surface of the diaper, wherein the dispensing openings are fluidly connected to the cavity to dispense the cream to the skin of the baby;
    a receiver opening extending through the interior surface of the diaper, wherein the receiver opening is fluidly connected to the cavity, wherein the receiver opening is larger in size than the dispensing openings, and wherein the receiver opening is adapted to removably receive the nozzle of the cream container for receiving the cream from the cream container; and
    a plurality of wet wipes positioned within the bag.

* * * * *